(12) United States Patent
Davis et al.

(10) Patent No.: US 11,369,272 B1
(45) Date of Patent: Jun. 28, 2022

(54) BROADBAND APPLICATOR FOR THERMOACOUSTIC SIGNAL GENERATION

(71) Applicant: ENDRA Life Sciences Inc., Ann Arbor, MI (US)

(72) Inventors: Christopher Nelson Davis, Ann Arbor, MI (US); Paolo Maccarini, Durham, NC (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 17/554,675

(22) Filed: Dec. 17, 2021

(51) Int. Cl.
*H01P 11/00* (2006.01)
*H01P 3/123* (2006.01)
*H01Q 13/06* (2006.01)
*A61B 5/00* (2006.01)

(52) U.S. Cl.
CPC ............ *A61B 5/0093* (2013.01); *H01P 3/123* (2013.01); *H01P 11/002* (2013.01); *H01Q 13/06* (2013.01)

(58) Field of Classification Search
CPC ...... A61B 5/0093; H01P 3/123; H01P 11/002; H01Q 13/06
See application file for complete search history.

(56) References Cited

U.S. PATENT DOCUMENTS

| | | | | |
|---|---|---|---|---|
| 6,097,264 A | * | 8/2000 | Vezmar | H01P 1/173 333/157 |
| 8,478,223 B2 | * | 7/2013 | Hiers | H01Q 13/0275 455/280 |
| 8,514,034 B2 | * | 8/2013 | Kang | H01P 3/123 333/211 |

* cited by examiner

*Primary Examiner* — Stephen E. Jones
*Assistant Examiner* — Kimberly E Glenn
(74) *Attorney, Agent, or Firm* — Stanley E. Jelic

(57) ABSTRACT

An RF applicator has an open-ended waveguide having an aperture and a dielectric cone extending through the aperture and is electrically connected to an RF source that is configured to generate RF energy pulses. A top fin is mounted to an inner top surface of the waveguide and comprises a conductive material, is electrically connected to the RF source, and has dimensions configured to optimize a bandwidth that the RF applicator applies to tissue. A bottom fin is mounted to an inner bottom surface of the waveguide and comprises a conductive material electrically isolated from the RF source, with dimensions configured to optimize a bandwidth that the RF applicator applies to tissue. A dielectric cone is inserted into the waveguide. A filler material between inner surfaces of the waveguide and the solid dielectric cone can fill gaps and has a dielectric constant similar to the dielectric cone.

20 Claims, 9 Drawing Sheets

BROADBAND APPLICATOR FOR THERMOACOUSTIC SIGNAL GENERATION

TECHNICAL FIELD

The present disclosure enables a broadband applicator for thermoacoustic signal generation. In particular, the broadband applicator structurally includes fins that are configured to optimize the bandwidth that the broadband applicator applies to tissue.

BACKGROUND

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. Also, in many instances, filters are employed to allow electromagnetic waves at some frequencies to pass and travel along the waveguides, while rejecting electromagnetic waves at other frequencies. One example is when propagating radio frequency (RF) waves, hollow, open-ended, conductive metal waveguides are often employed. In some instances to provide the desired filtering, these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

In order to direct RF pulses into the subject during thermoacoustic imaging, a radio frequency (RF) applicator employing a waveguide is coupled to tissue adjacent a region of interest (ROI) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, the composition of tissue within the subject, etc.

During fabrication of waveguides fitted with solid inserts, air gaps can form between the facing surfaces of the waveguides and the solid inserts. Unfortunately, the air gaps can change the frequency characteristics of the waveguides in an unpredictable manner. U.S. Pat. No. 10,682,059, filed Dec. 28, 2018, discusses a novel solution to the air gap problem and is incorporated by reference herein in its entirety.

SUMMARY

In overcoming the difficulties caused by air gaps, it was discovered that it is helpful to enable a broadband RF signal emanating from the applicator. Hence, embodiments herein describe an apparatus and method that generate a broadband RF signal that is optimized to match the characteristics of tissue.

In one embodiment, a radio frequency (RF) applicator comprises an open-ended hollow waveguide having an aperture therein; a conically-shaped dielectric extending through the aperture, wherein the conically-shaped dielectric is electrically connected to an RF source that is configured to generate RF energy pulses; a top fin mounted to an inner top surface of the open-ended hollow waveguide, wherein the top fin comprises a conductive material, is electrically connected to the RF source, and forms a quadrilateral shape with top fin dimensions that are configured to optimize a bandwidth that the RF applicator applies to tissue; a bottom fin mounted to an inner bottom surface of the open-ended hollow waveguide, wherein the bottom fin comprises a conductive material, is electrically isolated from the RF source, and forms a quadrilateral shape with bottom fin dimensions that are configured to optimize a bandwidth that the RF applicator applies to tissue; a solid dielectric insert within the open-ended hollow waveguide, the solid dielectric insert having recesses formed therein that are aligned with said aperture, said top fin, and said bottom fin; and a filler material between inner surfaces of the open-ended hollow waveguide and the solid dielectric insert to fill gaps therebetween, wherein the filler material has a dielectric constant that is similar to that of the solid dielectric insert.

The bottom fin may abuts the conically-shaped dielectric. The RF applicator may further comprise a feed probe extending from the conically-shaped dielectric. The RF applicator may further comprise a first side fin along an inner third surface of the open-ended hollow waveguide and a second side fin along an inner fourth surface of the open-ended hollow waveguide. The top fin may have a curved side, and the bottom fin may have a curved side. The conically-shaped dielectric may have a decreasing diameter extending from the inner bottom surface of the open-ended hollow waveguide.

In another embodiment, a waveguide for a radio frequency (RF) applicator comprises a housing having a conductive material; a first fin in the conductive material; a second fin in the conductive material; and a dielectric cone proximate to the second fin and electrically connected to an RF source.

The housing may expose the conductive material on a side. The first fin may be positioned along a first side of the housing. The second fin may be positioned along a second side of the housing opposed to the first side. The second fin may abut the dielectric cone. The first fin and second fin may comprise a conductive material. The waveguide may further comprise a feed probe extending from the dielectric cone, wherein the second fin is electrically isolated from the feed probe. The waveguide may further comprise a third fin along a third wall of the housing and a fourth fin along a fourth wall of the housing. The first fin may have a curved side, and the second fin has a curved side.

In yet another embodiment, a method for assembling a waveguide of an RF applicator comprises inserting a first fin and a second fin into a waveguide insert; inserting the waveguide insert into a housing having an open end that exposes the waveguide insert; inserting a conically-shaped dielectric into an aperture of the housing; and attaching a feed probe to the conically-shaped dielectric.

The first fin may be inserted on a first side of the waveguide insert, and the second fin may be inserted on a second side of the waveguide insert opposing the first side. The feed probe may be screwed into the waveguide insert.

The method may further comprise inserting a third fin and a fourth fin into the waveguide insert. The second fin may abut the conically-shaped dielectric.

It should be appreciated that this Summary is provided to introduce a selection of concepts in a simplified form that are further described below in the Detailed Description. This Summary is not intended to be used to limit the scope of the claimed subject matter.

BRIEF DESCRIPTION OF THE DRAWINGS

Embodiments will now be described more fully with reference to the accompanying drawings in which.

DETAILED DESCRIPTION

Embodiments herein describe a ceramic-filled waveguide antenna that is used to couple RF energy into tissue to generate thermoacoustic signals. In order to maximize the RF energy that is coupled to tissue, the ceramic-filled waveguide antenna must be matched to the impedance of an RF generator over the frequency of operation.

Generally, a radio frequency applicator comprises an open-ended, hollow waveguide having an aperture therein. A solid insert is positioned within the waveguide. The solid insert has a recess formed therein that is aligned with the aperture. Filler material is provided between facing surfaces of the waveguide and the insert to fill gaps therebetween. A radio frequency (RF) source extends through the aperture and into the recess and is configured to generate RF energy pulses.

The impedance of the antenna can change depending on the tissue composition to which the antenna is coupled. For example, antenna impedance can change depending on skin moisture and salinity, fat thickness under the skin, and temperature of the antenna (which is affected by skin temperature).

Manufacturing variations of the antenna components can cause difficulty in achieving a good match for the antenna over a specific frequency bandwidth depending on various tolerances stack-up for each antenna component. For example, for a hollow waveguide antenna with a solid insert, the distance (air gap) between the solid insert and the interior walls of the hollow waveguide antenna affects the impedance match between the hollow waveguide antenna and tissue.

Separate embodiments include a novel and non-obvious radio-frequency (RF) feed probe structure for the hollow waveguide antenna, designed to maximize the bandwidth of the antenna. This allows the antenna impedance to be less sensitive to the tissue variation and temperature. It also makes the bandwidth of the antenna less sensitive to variations in the antenna components. Separate embodiments further include a conical teflon (polymer) insert into the ceramic insert (dielectric) to uniformly vary impedance from a coaxial connector to the distributed feed structure.

Separate embodiments further include fins embedded into the ceramic to create a distributed feed structure for the waveguide antenna. The shape of the fins (radii of curvature, length, width, etc.) may be optimized to maximize the bandwidth of the waveguide antenna when coupled to tissue. As described herein, the edges of the fins may be straight or curved. In a curved fin embodiment, the edge may be convex or concave.

In a separate embodiment, the dielectric properties of the ceramic insert are also varied to increase the bandwidth of the antenna. For example, the ceramic insert may be non-uniform with varying permittivity in different sections of the insert.

Figure 1:
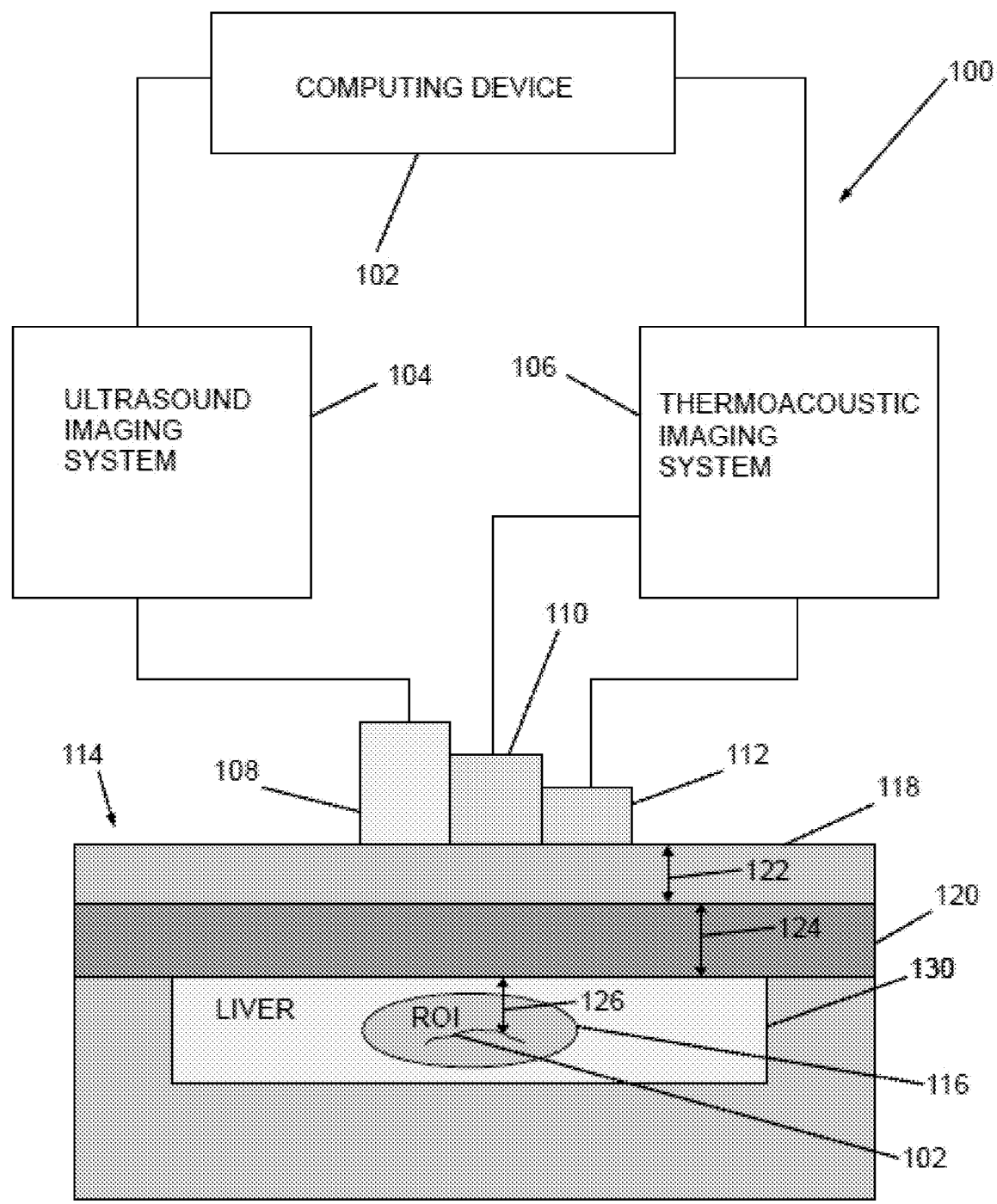
FIG. 1 is a block diagram of a thermoacoustic system, according to an embodiment.

Turning now to FIG. 1, an exemplary imaging system is shown and is generally identified by reference numeral 100. As can be seen, the imaging system 100 comprises a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest 116.

The programmed computing device 102 in this embodiment is a personal computer, server or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, is coupled to the computing device 102 for displaying one or more generated images that are based on ultrasound image data received from the ultrasound imaging system 104 and/or the thermoacoustic image data received from thermoacoustic imaging system 106. The programmed computing device 102 executes program code stored on the computer-readable system memory and/or other non-removable or removable computer-readable memory and performs methods according to the program code as will be described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest ROI, with different materials reflecting varying degrees of sound. Echoes that are received by the one or more ultrasound transducer arrays of the ultrasound transducer 108 are processed by the ultrasound imaging system 104 before being communicated as ultrasound image data to the computing device 102 for further processing and for presentation on the display device as ultrasound images that can be interpreted by an operator. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. Broadband radio-frequency (RF) applicator 112 may be housed together or separately from the thermoacoustic transducer 110. The broadband RF applicator 112 is configured to emit short pulses of RF energy that are directed into the region of interest ROI. In one embodiment, the broadband RF applicator 112 has a frequency between about 10 Mhz and 100 GHz and has a pulse duration between about 0.1 nanoseconds and 10 microseconds. The broadband RF applicator 112 emits RF energy pulses to materials or tissue within the region of interest 116 to induce acoustic pressure waves (thermoacoustic multi-polar signals) within the region of interest 116 that are detected by the thermoacoustic transducer 110. Acoustic pressure waves that are detected by the thermoacoustic transducer 110 are processed and communicated as thermoacoustic image data to the computing device 102 for further processing and for presentation on the display device as thermoacoustic images that can be interpreted by the operator.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), region of interest 116 contains blood vessel 102 and is located within a liver 130 of a human or animal body (patient) 114. Patient 114 comprises a subcutaneous fat layer 118 and muscle layer 120 adjacent to liver 130. Distances shown: $d_f$ is the subcutaneous fat thickness of the patient 122, $d_m$ is the muscle thickness of the patient 124, $d_b$ is distance from the boundary between the muscle and the liver to the center of the blood vessel 126.

Figure 2:
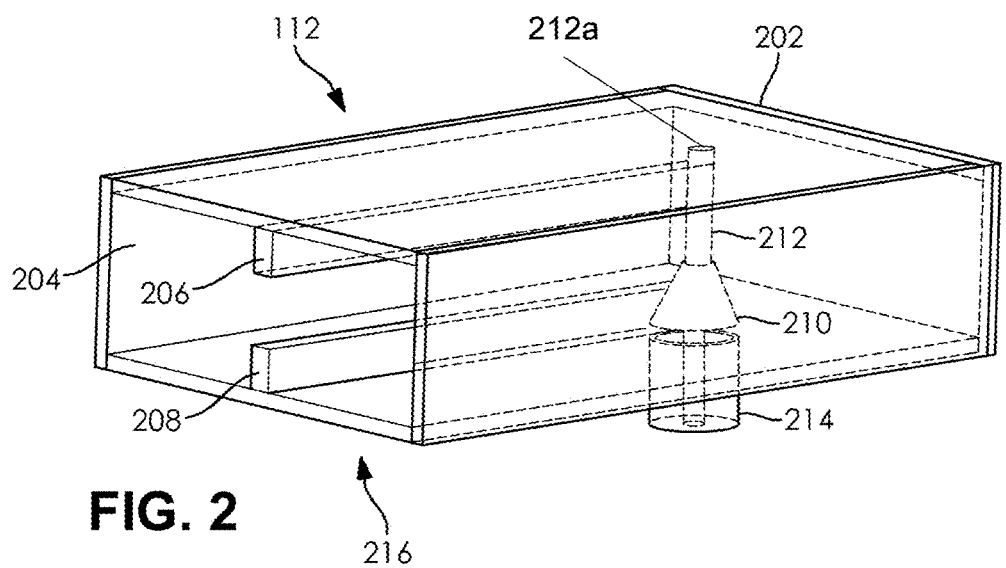
FIG. 2 is a perspective view of a broadband applicator for thermoacoustic signal generation, according to an embodiment.

FIG. 2 is a perspective view of a broadband applicator for thermoacoustic signal generation. Shown are broadband RF applicator 112, waveguide 202, waveguide insert 204, top fin 206, bottom fin 208, and solid dielectric cone 210, feed probe 212, and aperture 214. The waveguide 202 has an open window 216 from which RF energy emanates and presses against a patient/subject. In one configuration, the applicator has metal walls on each side, except for side of the open window 216, thereby allowing exposure of the dielectric within the applicator. The aperture 214 is a coaxial feed for an RF source. The aperture 214 extends through a wall of the waveguide 202 and couples to the dielectric cone 210.

Figure 3:
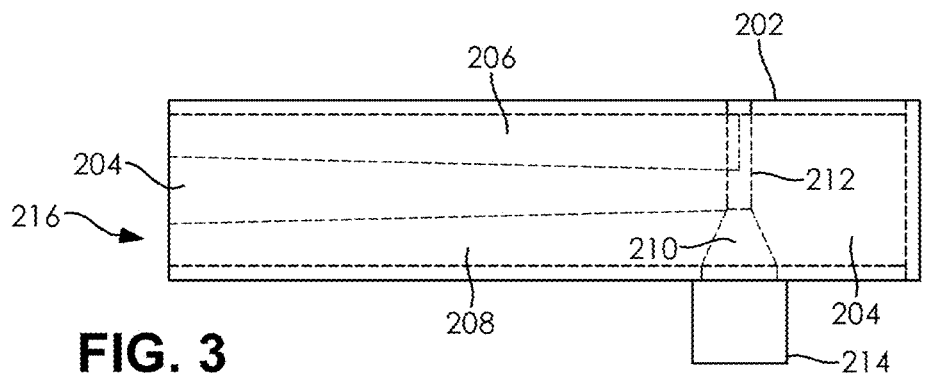
FIG. 3 is a cross sectional side-view of a broadband applicator for thermoacoustic signal generation, according to an embodiment.

FIG. 3 is a cross section side-view of a broadband applicator for thermoacoustic signal generation. Shown are broadband RF applicator 112, waveguide 202, waveguide insert 204, top fin 206, bottom fin 208, and solid dielectric cone 210, feed probe 212, and aperture 214. The waveguide insert 204 may be a ceramic material, which is inserted into a metal hosing. In one embodiment, the ceramic material may have a real relative permittivity of greater than 10, such as between about 57 and 63, and a loss tangent less than 0.01. In one or more embodiments, the filler material has a melting point in the range of from about 40 and 120 degrees Centigrade. The filler material may be in the form of a ceramic wax composite. The ceramic wax composite may have a real relative permittivity between about 30 and 50 and an imaginary relative permittivity between about 2 and 7. For example, the ceramic wax composite may comprise 69% to 80% by weight titanium dioxide, 10% to 15% by weight wax and 4% to 13% by weight graphite. In one or more embodiments, the filler material is one of: (i) a ceramic wax composite; (ii) a conductive paste; (iii) a conductive grease; and (iv) a ceramic powder and gel wax mixture.

The waveguide insert 204 may be configured to receive the top fin 206 and bottom fin 208. For example, slots may be created in the waveguide insert 204 that receive the top fin 206 and bottom fin 208. The waveguide insert 204 may also have a hole configured for the feed probe 212.

Figure 4:
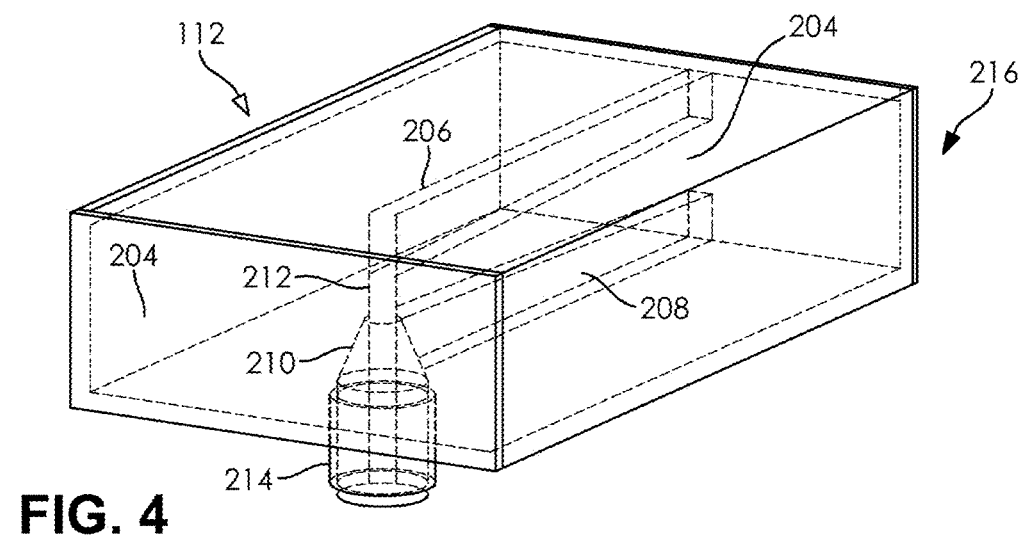
FIG. 4 is a rear-perspective view of a broadband applicator for thermoacoustic signal generation, according to an embodiment.

FIG. 4 is a rear-perspective view of a broadband applicator for thermoacoustic signal generation. Shown are broadband RF applicator 112, waveguide 202, waveguide insert 204, top fin 206, bottom fin 208, and solid dielectric cone 210, feed probe 212, and aperture 214.

The top fin 206 electrically connects to the feed probe 212. A hole of top fin 206 may receive a thread of feed probe 212. The bottom fin 208 is isolated from the feed probe 212. The bottom fin 208 is flush to an edge of the dielectric cone 210.

Figure 5:
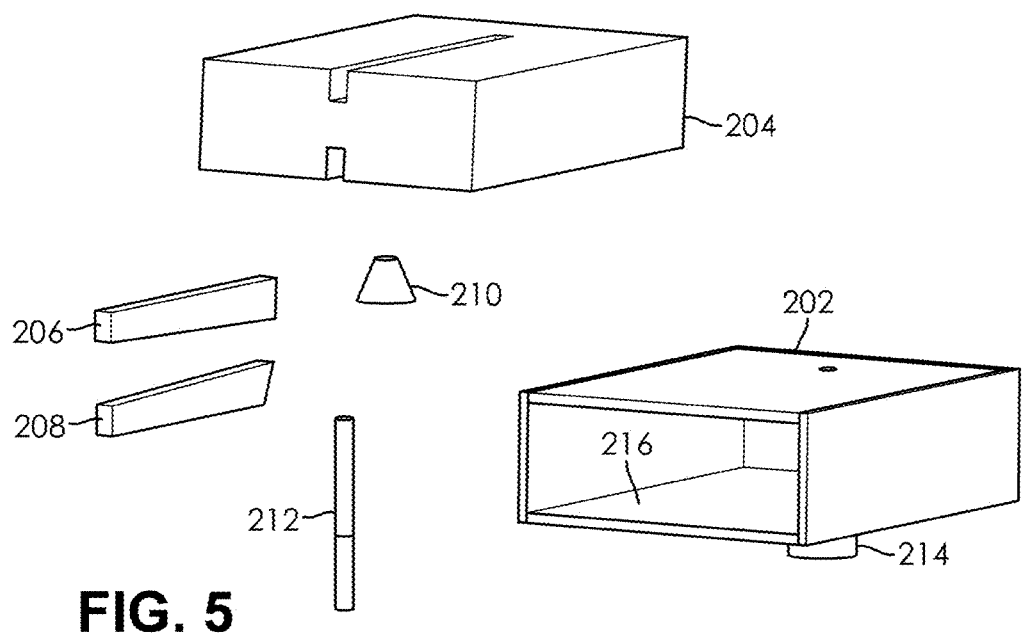
FIG. 5 is an exploded perspective view of a broadband applicator for thermoacoustic signal generation, according to an embodiment.

FIG. 5 is an exploded perspective view of a broadband applicator for thermoacoustic signal generation. Shown are broadband RF applicator 112, waveguide 202, waveguide insert 204, top fin 206, bottom fin 208, and solid dielectric cone 210, feed probe 212, and aperture 214.

Figure 6:
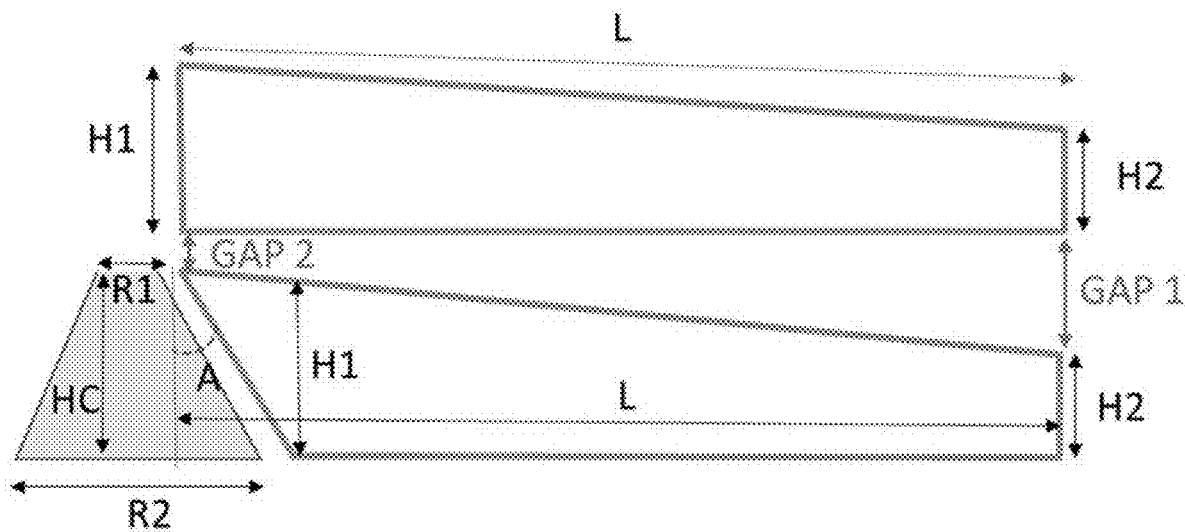
FIG. 6 shows a cross-sectional side-view of a broadband applicator with dimensions of the top fin, bottom fin, and dielectric cone, according to an embodiment.

FIG. 6 shows example dimensions of top fin 206, bottom fin 208, and dielectric cone 210, according to an embodiment. The top fin 206 may be a conductive material, such as aluminum, and may be electrically connected to the RF source. In this illustrative embodiment, the top fin 206 is a quadrilateral structure defined by a height H1 near the dielectric cone 210 and a height H2 near the open window 216. The top fin 206 has a length L extending from an upper edge of the dielectric cone 210 to the open window 216. In one example, the top fin 206 has dimensions of height H1 is 8.025 mm, height H2 is 5.275 mm, and length L is 69.85 mm. Height H1 may be about 8 mm, between about 6 and 10 mm, or between about 4 and 12 mm. Height H2 may be about 5 mm, between about 4 and 7 mm, or between about 2 and 9 mm. Length L may be about 70 mm, between about 65 and 75 mm, or between about 60 and 80 mm. These dimensions are merely illustrative and may vary from the description herein. The heights H1, H2 and length L may be optimized to maximize the bandwidth over which the applicator is matched on tissue.

The bottom fin 208 may be a conductive material, such as aluminum, that is isolated from the RF source. The bottom fin 208 may be a quadrilateral structure defined by a height H1 near the dielectric cone 210 and a height H2 near the open window 216. The bottom fin 208 has a length L extending from the upper edge of the dielectric cone 210 to the open window 216. In one example, the bottom fin 208 has dimensions of height H1 is 8.025 mm, height H2 is 5.275 mm, and length L is 69.85 mm. Height H1 may be about 8 mm, between about 6 and 10 mm, or between about 4 and 12 mm. Height H2 may be about 5 mm, between about 4 and 7 mm, or between about 2 and 9 mm. Length L may be about 70 mm, between about 65 and 75 mm, or between about 60 and 80 mm. These dimensions are merely illustrative and may vary from the description herein. The heights H1, H2 and length L may be optimized to maximize the bandwidth over which the applicator is matched on tissue. In the illustrative embodiment, top fin 206 and bottom fin 208 have the same dimensions for height H1, height H2, and length L.

The bottom fin 208 has a side along the dielectric cone 210 an angle A with a vertical axis of the dielectric cone 210. In one example, the angle A is 20.5 degrees. Angle A may be about 21 degrees, between about 19 to 22 degrees, or between about 17 to 24 degrees.

The dielectric cone 210 may abut flush with the bottom fin 208. The dielectric cone may have a height HC, upper diameter R1, and lower diameter R2. In one example, height HC is 8.025 mm, upper diameter R1 is 2 mm, and lower diameter R2 is 5 mm. Height HC may be about 8 mm, between about 7 to 9 mm, or between about 5 to 11 mm. Upper diameter R1 may be about 2 mm, between about 1.5 to 2.5 mm, or between about 1 to 3 mm. Lower diameter R2 may be about 5 mm, between about 4 to 6 mm, or between about 3 to 7 mm. These dimensions are merely illustrative and may vary from the description herein. The diameters R1, R2 and height HC may be selected based on the angle A and height H1 of the bottom fin 208. R1 may be slightly larger than the feed probe, e.g., 0.5 mm larger.

When top fin 206, bottom fin 208, and dielectric cone 210 are positioned, the top fin 206 and bottom fin 208 have a gap that increases in size away from the dielectric cone 210 and toward the open window 216. The size of the gap may be varied to control impedance. A GAP 1 proximate the open window 216 will be larger than a GAP 2 near the dielectric cone 210. In one example, GAP 1 is 8.5 mm, and GAP 2 is 3 mm. GAP 1 may be between about 1 mm and 16 mm, including 5 mm, 7 mm, 8.5 mm, 10 mm, and 15 mm. GAP 1 may also range between about 0.5 mm and 20 mm. GAP 2 may be between about 1 mm and 12 mm, including 2 mm, 3 mm, 5 mm, and 7 mm. GAP 2 may also be between about 0.5 mm and 15 mm. These dimensions are merely illustrative and may vary from the description herein.

In an example, the dielectric cone 210 may be made of Teflon, which has a different permittivity than the waveguide insert 204. For example, the dielectric cone 210 may have a permittivity of 2, whereas the waveguide insert 204 may have a permittivity of 60. The dielectric cone 210 may act as a spacer by continuously varying space with the feed probe, thereby changing impedance. The varied spacing from diameter R2 to diameter R1 can give a transition of impedance to match.

Figure 7:
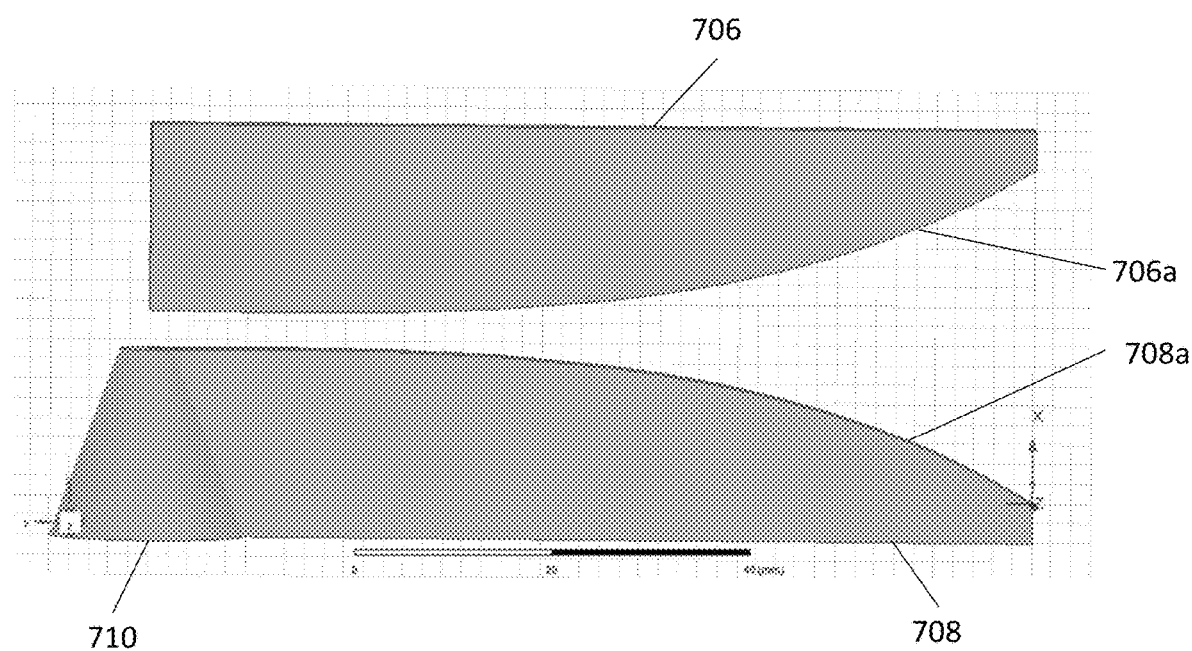
FIG. 7 shows a cross-sectional side view of a broadband applicator having a curved top fin and a curved bottom fin, according to an embodiment.

FIGS. 2-6 show a configuration of the top fin 206 and bottom fin 208 having straight edges. It is intended that the top fin and bottom fin may have other configurations. In another embodiment, FIG. 7 shows a top fin 706 and a bottom fin 708. Top fin 706 has a lower curved edge 706a. Bottom fin 708, shown flush against dielectric cone 710, has an upper curved edge 708a. In this embodiment, lower curved edge 706a and upper curved edge 708a are substantially parallel near the dielectric cone 710. The lower curved edge 706a and the upper curved edge 708a diverge toward to an open window.

The dielectric cone 210 may provide a uniform transition in impedance form a coaxial cable to a top of the bottom fin 208 in the waveguide. The dielectric cone may be useful to increase the applicator bandwidth as compared to an embodiment that has fins without a dielectric cone.

Figure 8:
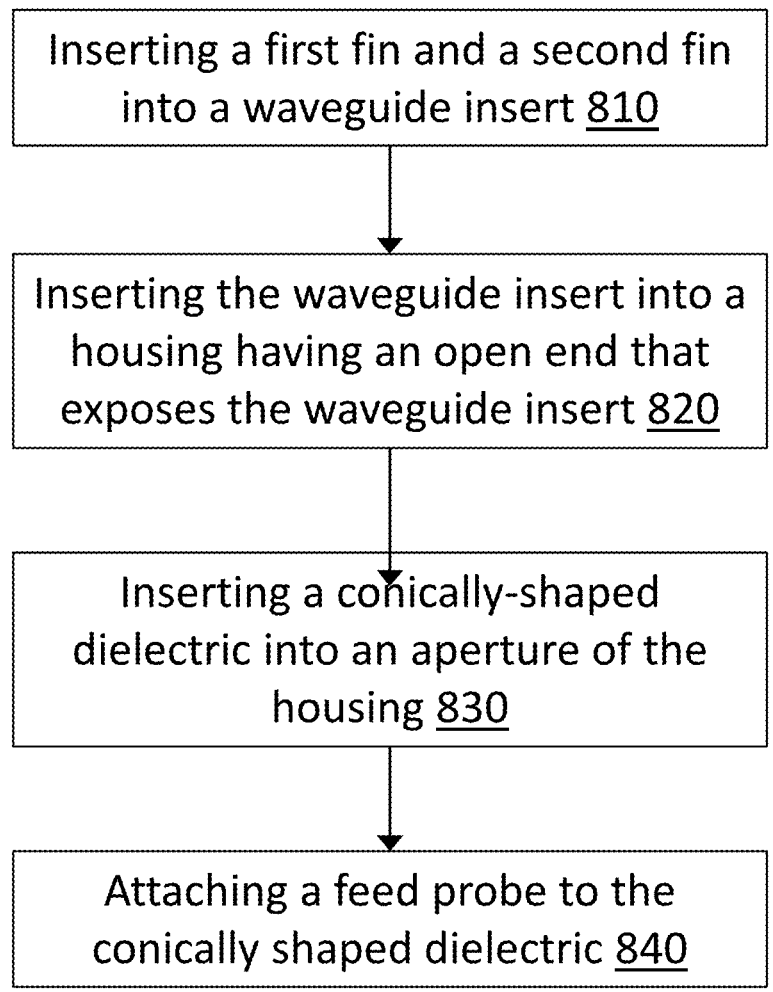
FIG. 8 shows a method of assembly of a waveguide of an RF applicator, according to an embodiment.

In an example method of assembling the waveguide, top fin 206 and bottom fin 208 may be inserted into waveguide insert 204. The waveguide insert 204 may then be inserted into waveguide 202. The dielectric cone 210 may be inserted through aperture 214 into the waveguide 202. In one configuration, the feed probe 212 may be a screwed into a location 212a of the waveguide 202. In another configuration, the feed probe 212 is secured with conductive paste. In an illustrative embodiment shown in FIG. 8, a method for assembling a waveguide of an RF applicator comprises: in step 810, inserting a first fin and a second fin into a waveguide insert; in step 820, inserting the waveguide insert into a housing having an open end that exposes the waveguide insert; in step 830, inserting a conically-shaped dielectric into an aperture of the housing; and in step 840, attaching a feed probe to the conically-shaped dielectric.

Although the illustrative embodiments show a top fin and a bottom fin in the waveguide, it is intended that the waveguide may be configured with alternative or additional fins in other locations of the waveguide, such as the side walls or corners. Also, although the illustrative embodiments show two fins, it is intended that the waveguide may contain two or more fins.

RF characteristics are used to determine the parameter of interest of the material. A voltage standing wave ratio (VSWR) may be calculated as a measure of how efficiently RF power is being transmitted from the RF applicator. Generally, the VSWR is calculated by monitoring the RF forward and reflected power of the RF energy pulses. The RF forward power is the power of the RF energy pulses emitted by the RF applicator. The RF reflected power is the power of the RF energy pulses that are reflected back to the RF applicator. Using the RF forward and reflected powers, the VSWR is calculated. The system may measure forward and reflected RF signal power along the RF signal path, then may calculate an S11 parameter (reflection coefficient or return loss) measurement as a ratio of the reflected RF signal power to the forward RF signal power and may calculate the VSWR measurement from the S11 parameter measurement.

Figure 9:
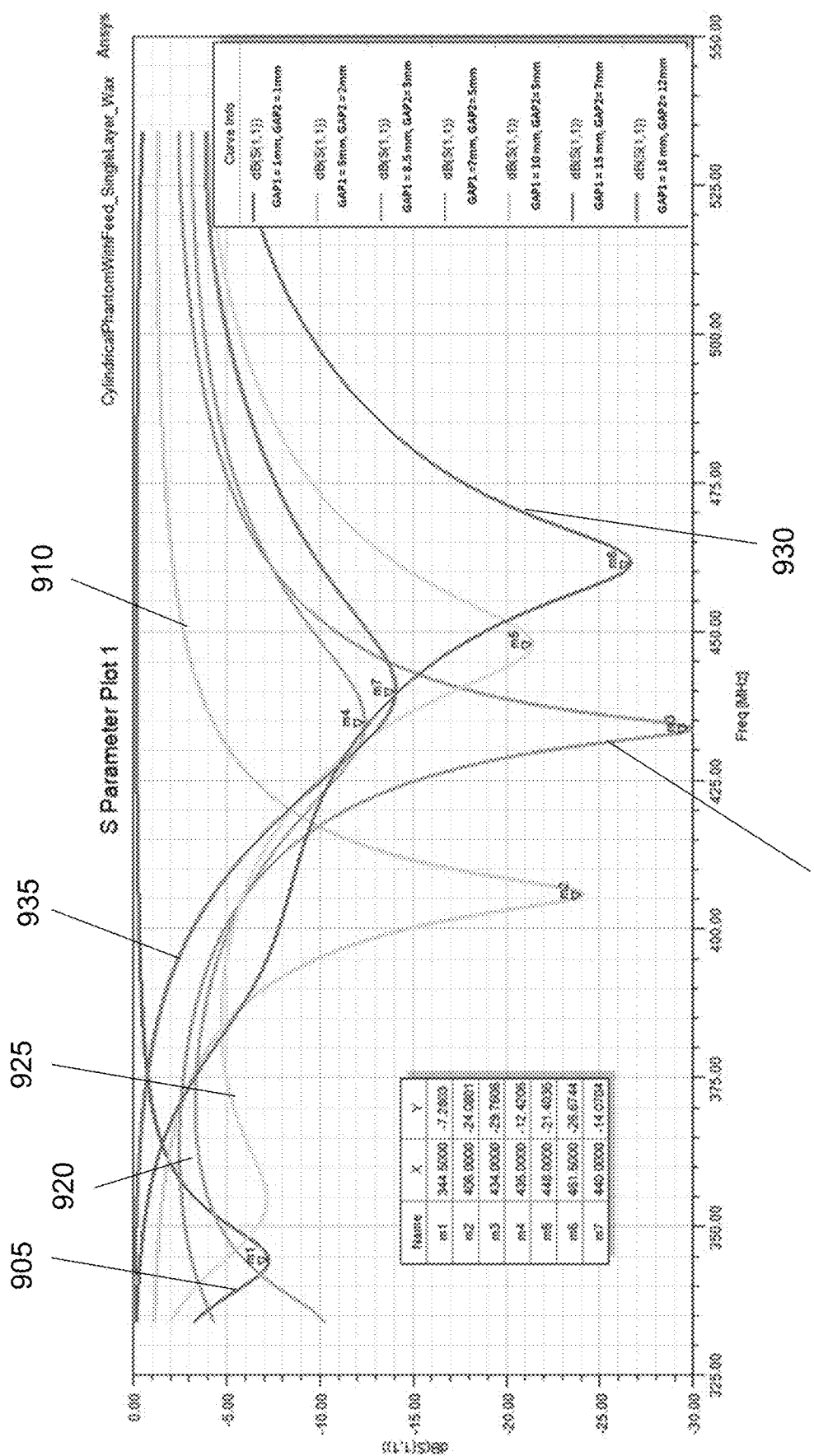
FIG. 9 shows a graph depicting a variation of S11 on tissue with geometric changes of a top fin and a bottom fin, according to an embodiment.

FIG. 9 is a graph depicting a variation of S11 on tissue with geometric changes of a top fin and a bottom fin. In particular, the variation reflects changes in gaps (e.g., GAP 1 and GAP 2 shown in FIG. 6). The variations shown include a line 905 representing GAP 1 is 1 mm and GAP 2 is 1 mm, a line 910 representing GAP 1 is 5 mm and GAP 2 is 2 mm, a line 915 representing GAP 1 is 8.5 mm and GAP 2 is 3 mm, a line 920 representing GAP 1 is 7 mm and GAP 2 is 5 mm, a line 825 representing GAP 1 is 10 mm and GAP 2 is 5 mm, a line 930 representing GAP 1 is 15 mm and GAP 2 is 7 mm, and a line 935 representing GAP 1 is 16 mm and GAP 2 is 12 mm.

Figure 10:
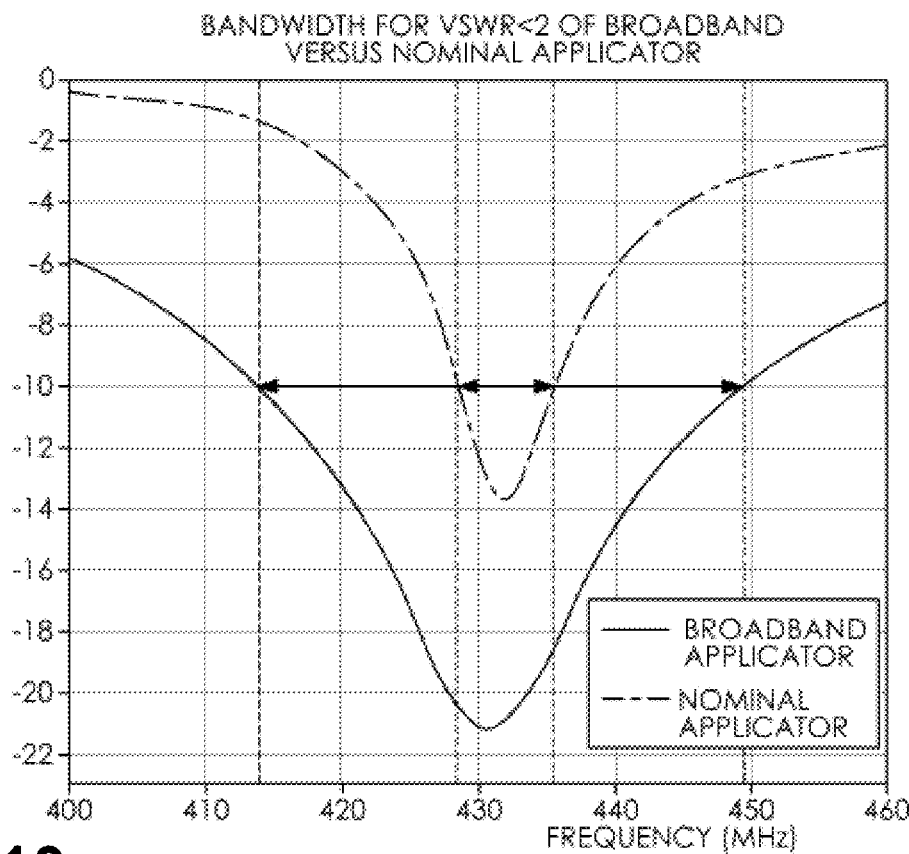
FIG. 10 shows a sample bandwidth for a VSWR<2 of a broadband applicator versus a nominal applicator, according to an embodiment.

FIG. 10 shows sample bandwidth for a VSWR<2 of a broadband applicator (solid line) versus a nominal applicator (dashed line). In this embodiment, it may be desired to have a bandwidth below –10, and the broadband applicator exhibits more bandwidth below –10. FIG. 10 is intended to illustrate that an example of the broadband applicator has increased bandwidth below a desired threshold.

Figure 11:
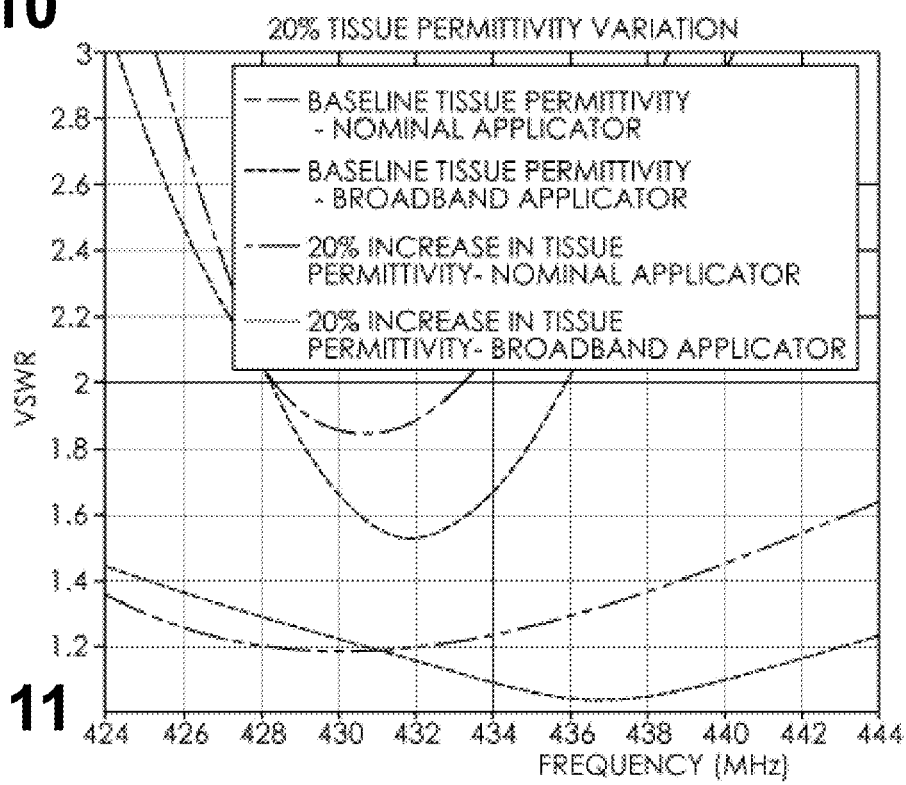
FIG. 11 shows a sample effect of a 20% tissue permittivity variation, according to an embodiment.

FIG. 11 shows a sample effect of a 20% tissue permittivity variation. In this illustration for an example broadband applicator and nominal applicator, the VSWR is still below 2 for the broadband applicator and nominal applicator when the tissue permittivity changes by 20%.

Figure 12:
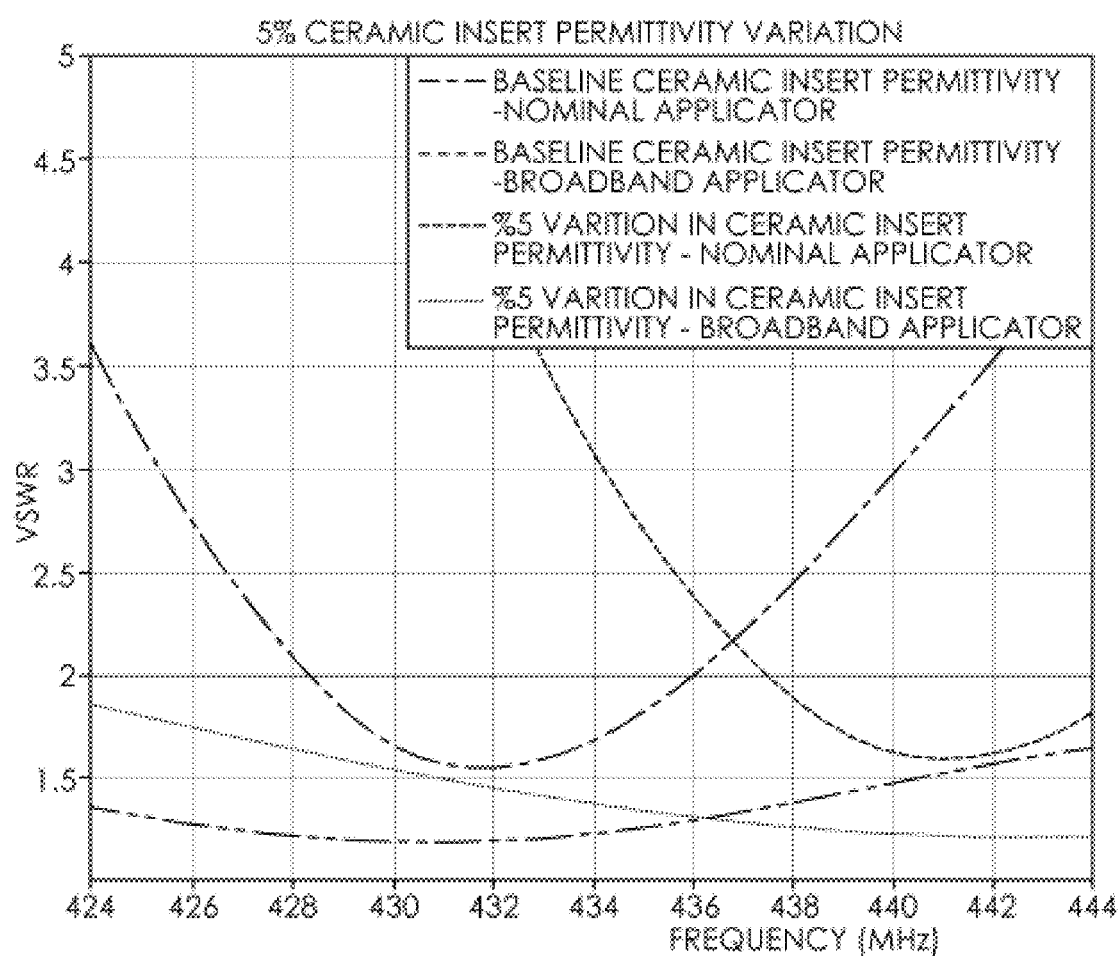
FIG. 12 shows a sample effect of a 5% tissue permittivity variation, according to an embodiment.

FIG. 12 shows a sample effect of a 5% tissue permittivity variation. FIG. 12 is similar to FIG. 11 but utilizes a ceramic insert, which may be desirable for manufacturability. In this illustration, the VSWR still remains below 2.

Although embodiments have been described above with reference to the accompanying drawings, those of skill in the art will appreciate that variations and modifications may be made without departing from the scope thereof as defined by the appended claims.

What is claimed is:

1. A radio frequency (RF) applicator comprising:
    an open-ended hollow waveguide having an aperture therein;
    a conically-shaped dielectric extending through the aperture, wherein the conically-shaped dielectric is electrically connected to an RF source that is configured to generate RF energy pulses;
    a top fin mounted to an inner top surface of the open-ended hollow waveguide, wherein the top fin comprises a conductive material, is electrically connected to the RF source, and forms a quadrilateral shape with top fin dimensions that are configured to optimize a bandwidth that the RF applicator applies to tissue;
    a bottom fin mounted to an inner bottom surface of the open-ended hollow waveguide, wherein the bottom fin comprises a conductive material, is electrically isolated from the RF source, and forms a quadrilateral shape with bottom fin dimensions that are configured to optimize a bandwidth that the RF applicator applies to tissue;
    a solid dielectric insert within the open-ended hollow waveguide, the solid dielectric insert having recesses formed therein that are aligned with said aperture, said top fin, and said bottom fin; and
    a filler material between inner surfaces of the open-ended hollow waveguide and the solid dielectric insert to fill gaps therebetween, wherein the filler material has a dielectric constant that is similar to that of the solid dielectric insert.

2. The RF applicator of claim 1, wherein the bottom fin abuts the conically-shaped dielectric.

3. The RF applicator of claim 1, further comprising a feed probe extending from the conically-shaped dielectric.

4. The RF applicator of claim 1, further comprising a first side fin along an inner third surface of the open-ended hollow waveguide and a second side fin along an inner fourth surface of the open-ended hollow waveguide.

5. The RF applicator of claim 1, wherein the top fin has a curved side, and the bottom fin has a curved side.

6. The RF applicator of claim 1, wherein the conically-shaped dielectric has a decreasing diameter extending from the inner bottom surface of the open-ended hollow waveguide.

7. A waveguide for a radio frequency (RF) applicator comprising:
    a housing having a conductive material;
    a first fin in the conductive material;
    a second fin in the conductive material; and
    a dielectric cone proximate to the second fin and electrically connected to an RF source.

8. The waveguide of claim 7, wherein the housing exposes the conductive material on a side.

9. The waveguide of claim 8, wherein the first fin is positioned along a first side of the housing.

10. The waveguide of claim 9, wherein the second fin is positioned along a second side of the housing opposed to the first side.

11. The waveguide of claim 8, wherein the second fin abuts the dielectric cone.

12. The waveguide of claim 8, wherein the first fin and second fin comprise a conductive material.

13. The waveguide of claim 8, further comprising a feed probe extending from the dielectric cone, wherein the second fin is electrically isolated from the feed probe.

14. The waveguide of claim 8, further comprising a third fin along a third wall of the housing and a fourth fin along a fourth wall of the housing.

15. The waveguide of claim 8, wherein the first fin has a curved side, and the second fin has a curved side.

16. A method for assembling a waveguide of a radio frequency (RF) applicator, the method comprising:
    inserting a first fin and a second fin into a waveguide insert;
    inserting the waveguide insert into a housing having an open end that exposes the waveguide insert;
    inserting a conically-shaped dielectric into an aperture of the housing; and
    attaching a feed probe to the conically-shaped dielectric.

17. The method of claim 16, wherein the first fin is inserted on a first side of the waveguide insert, and the second fin is inserted on a second side of the waveguide insert opposing the first side.

18. The method of claim 16, wherein the feed probe is screwed into the waveguide insert.

19. The method of claim 16, further comprising inserting a third fin and a fourth fin into the waveguide insert.

20. The method of claim 16, wherein the second fin abuts the conically-shaped dielectric.

* * * * *